United States Patent
Rieker et al.

(10) Patent No.: US 10,473,818 B2
(45) Date of Patent: *Nov. 12, 2019

(54) HUB AND SPOKE SYSTEM FOR DETECTING AND LOCATING GAS LEAKS

(71) Applicants: The Regents of the University of Colorado, Denver, CO (US); Government of the United States of America as represented by the Secretary of Commerce, Gaithersburg, MD (US)

(72) Inventors: Gregory B. Rieker, Boulder, CO (US); Ian Coddington, Boulder, CO (US); Nathan R. Newbury, Boulder, CO (US); Kuldeep Prasad, Vienna, VA (US); Anna Karion, Bethesda, MD (US)

(73) Assignees: The Regents of the University of Colorado, a body corporate, Denver, CO (US); Government of the United States of America as represented by the Secretary of Commerce, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/263,540

(22) Filed: Jan. 31, 2019

(65) Prior Publication Data
US 2019/0170900 A1 Jun. 6, 2019

Related U.S. Application Data

(63) Continuation of application No. 15/152,543, filed on May 11, 2016, now Pat. No. 10,228,490.
(Continued)

(51) Int. Cl.
*G01W 1/00* (2006.01)
*G01M 3/20* (2006.01)
*G01J 3/42* (2006.01)

(52) U.S. Cl.
CPC ............... *G01W 1/00* (2013.01); *G01J 3/42* (2013.01); *G01M 3/202* (2013.01)

(58) Field of Classification Search
CPC ............ G01J 3/42; G01M 3/202; G01W 1/00
See application file for complete search history.

(56) References Cited

U.S. PATENT DOCUMENTS 8,564,785 B2 10/2013 Newbury et al.
8,595,020 B2 11/2013 Marino
(Continued)

OTHER PUBLICATIONS

Mancini et al., 'Remote Sensing, Using unmanned Aerial Vehicle (UAV) for high resolution Reconstruction of Tomography: The structure from Motion Approach on Coastal Environments,' 2013, Remote Sensing, vol. 5, pp. 6880-6898. (Year: 2013).*
Hashmonay et al. (1999) "Computed tomography of air pollutants using radial scanning path-integrated optical remote sensing," Atmospheric Environment, 33, pp. 267-274.
(Continued)

*Primary Examiner* — Elias Desta
(74) *Attorney, Agent, or Firm* — Lathrop Gage LLP

(57) ABSTRACT

A system for detecting gas leaks and determining their location and size. A data gathering portion of the system utilizes a hub and spoke configuration to collect path-integrated spectroscopic data over multiple open paths around an area. A processing portion of the system applies a high-resolution transport model together with meteorological data of the area to generate an influence function of possible leak locations on gas detector measurement paths, and applies an inversion model to the influence function and the spectroscopic data to generate gas source size and location.

20 Claims, 5 Drawing Sheets

Related U.S. Application Data

(60) Provisional application No. 62/160,163, filed on May 12, 2015.

(56) References Cited

U.S. PATENT DOCUMENTS

| | | |
|---|---|---|
| 9,194,744 B2 | 11/2015 | Yost et al. |
| 10,228,490 B2 * | 3/2019 | Rieker .................... G01W 1/00 |
| 2005/0142581 A1 * | 6/2005 | Griffey ................. C12N 15/111 |
| | | 435/6.11 |
| 2018/0003641 A1 | 1/2018 | Gamache |

OTHER PUBLICATIONS

Flesch et al. (2005) "Estimating gas emissions from a farm with an inverse-dispersion technique," Atmospheric Environment, 39, pp. 4863-4874.

Hashmonay et al. (1999) "Localizing Gaseous Fugitive Emission Sources by Combining Real-Time Optical Remote Sensing and Wind Data," Air & Waste Manage. Assoc., 49, pp. 1374-1379.

Lan et al. (2015) "Characterizing Fugitive Methane Emissions in the Barnett Shale Area Using a Mobile Laboratory," Environ. Sci. Technol., 49, pp. 8139-8146.

Thomson et al. (2007) "An improved algorithm for locating a gas source using inverse methods," Atmospheric Environment, 41, pp. 1128-1134.

Levine et al. (2016) "The detection of carbon dioxide leaks using quasi-tomographic laser absorption spectroscopy measurements in variable wind," Atmos. Meas. Tech., 9, pp. 1627-1636.

* cited by examiner

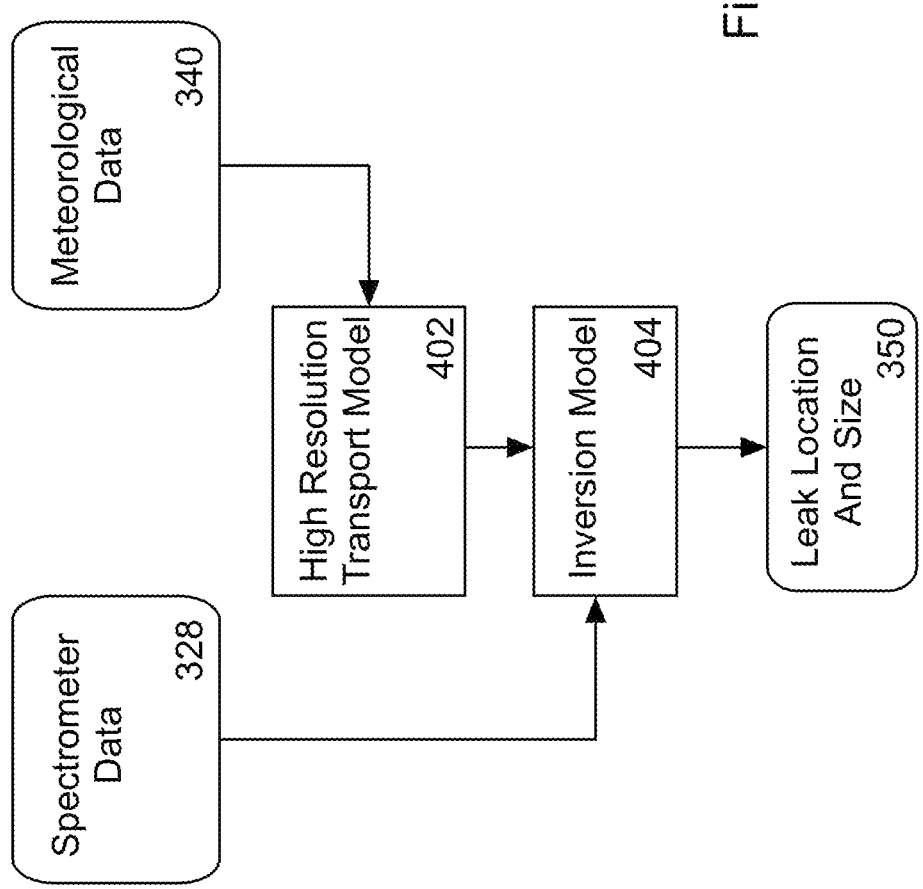

HUB AND SPOKE SYSTEM FOR DETECTING AND LOCATING GAS LEAKS

CROSS-REFERENCE TO RELATED APPLICATIONS

This application is a continuation of U.S. patent application Ser. No. 15/152,543, filed May 11, 2016, which claims priority to U.S. Provisional Patent Application Ser. No. 62/160,163, filed May 12, 2015. Each of these applications is incorporated herein by reference. U.S. Pat. No. 8,564,785, issued Oct. 22, 2013, is also incorporated herein by reference.

STATEMENT REGARDING FEDERALLY SPONSORED RESEARCH OR DEVELOPMENT

This invention was made with government support under grant number DE-AR0000539 awarded by the United States Department of Energy. The government has certain rights in the invention.

FIELD

The present invention relates to apparatus and methods for detecting and locating gas leaks. In particular, the present invention relates to a hub and spoke spectroscopy system for detecting and locating methane leaks.

BACKGROUND

Current open-path techniques that are capable of measuring methane leaks over long paths include diode laser-based absorption systems, LIDAR systems, and FTIR-based systems. Mobile FTIR systems suffer from low wavelength resolution (large instrument distortion), and have thus far only demonstrated ~5-10% measurement uncertainty for trace greenhouse gases (GHGs), which is far too great to detect, locate, and size methane leaks at kilometer scale standoff distances.

Diode laser-based systems and LIDAR systems focus on measurements of a few wavelengths around a single absorption feature of methane (or a wavelength sweep over 1-2 features). High precision, long-term stability, and accuracy is difficult due to turbulence-induced laser intensity fluctuations and interference from overlapping absorption of other molecules that are not included in spectral fits. Even techniques which rely on detection of phase shifts induced by absorption features (instead of direct absorption) must account for phase shift induced by any absorbing component in the beam path and neighboring absorption features.

Sparse wavelength laser systems also do not typically measure other species, temperature, pressure, or water vapor. A simultaneous measurement of water vapor, temperature, and pressure is desirable for correcting measured methane mole fractions to dry-air mole fractions, to account for time varying dilution effects of water vapor change on the apparent concentration of methane. In addition, water vapor, temperature and pressure influence methane absorption feature shape, which is important when fitting the absorption features to accurately extract the methane mole fraction for calibration-free operation.

Many previous methane studies near oil and gas operations were performed with commercial cavity-ringdown laser spectrometers (CRDS) either fixed, or mounted on vehicles and aircraft. These spectrometers enable very high sensitivity with short measurement times, but require periodic calibration, and are expensive. For specific leak detection with inversion techniques, the sensors either require an operator (pilot or driver) or a network of multiple expensive sensors and common calibration.

Several other types of low-cost in-situ sensors for methane exist. Some focus on making flux measurements because they are not stable over long periods of time. Others lack the measurement precision needed to identify smaller leaks or need to be calibrated often and corrected for effects of temperature, pressure, humidity, or other interfering species (possibly requiring regular access to the well pad). Other in-situ sensors with lower cost than CRDS sensors still require either an operator to get spatial information or multiple sensors. Using multiple sensors requires intercalibration and inter-comparability between the various sensors to correct for background fluctuations in methane with a remote background sensor or to compare methane concentration between sites. In a distributed system, each sensor may require power and communication.

A need remains in the art for apparatus and methods for detecting gas leaks capable of sensitivity, accuracy, lack of calibration, and multi-species operation over kilometer-scale paths.

SUMMARY OF THE EMBODIMENTS

It is an object of the present invention to provide apparatus and methods for detecting gas leaks capable of sensitivity, accuracy, calibration-free operation, and multi-species detection over kilometer-scale paths.

A low cost dual comb spectrometer design uses the method of deploying a line of sight, broadband, laser absorption sensor to locate and size trace gas leaks. An embodiment of the present invention includes an open path spectrometer gas detector combined with a high-resolution transport model and an inversion model to detect and locate gas leaks.

A system according to the present invention determines the location and size of a gas source within an area by providing a spectrometer gas detector, collecting path-integrated spectroscopic data over multiple open paths around the area with the detector, collecting meteorological data related to the area, applying a high resolution transport model together with meteorological data to generate an influence function of potential source locations on gas detector measurement paths, and applying an inversion model to the influence function and spectroscopic data to generate gas source size and location. The spectrometer might be based on a dual comb spectrometer. In a preferred embodiment, the high-resolution transport model is a large eddy simulation. The system might employ a number of reflectors, such as retroreflectors arrayed around the area, or a mobile reflector, for example on a UAV. The meteorological data might be measured onsite or provided by a simulation model of the area. Some embodiments use Kalman filtering to update the inversion model.

The system might include a telescope for transmitting laser beams and receiving the reflected beams, and a gimbal for orienting the telescope to scan the area.

BRIEF DESCRIPTION OF THE DRAWINGS

FIG. 1A (Prior Art) is a schematic block diagram illustrating the process of passing two frequency combs through a gas and detecting the resulting light. FIG. 1B (Prior Art) shows the two frequency combs after the light passes through the gas. FIG. 1C (Prior Art) illustrates the resulting heterodyne interference signals.

FIG. 4A is a flow diagram illustrating a general embodiment of the signal processing portion of the present invention.

DETAILED DESCRIPTION OF THE INVENTION

Figure 1A:
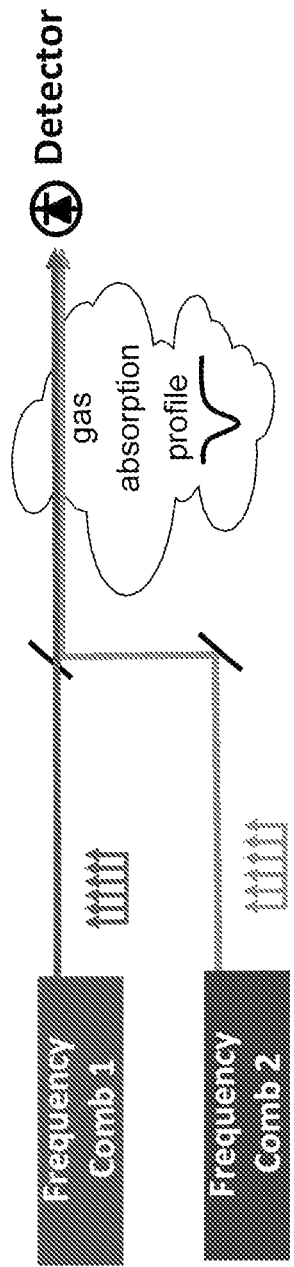
FIGS. 1A-1C (Prior Art) illustrate the operation of a dual comb spectroscopy (DCS) system that is useful in the data gathering portion of the present invention.
Figure 1B:
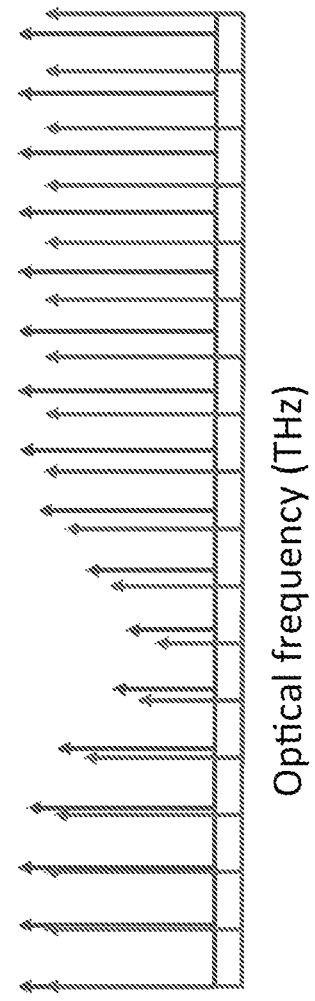
Figure 1C:
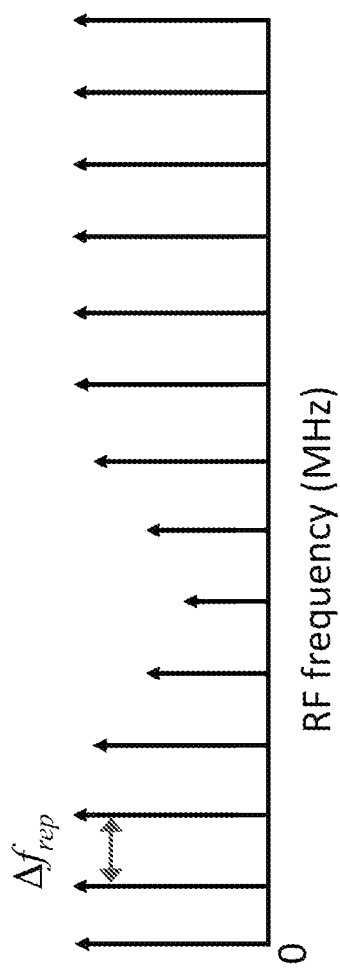

FIGS. 1A-1C (Prior Art) illustrate the operation of a dual comb spectroscopy (DCS) system that is useful in the gas detection portion of the present invention. FIG. 1A (Prior Art) is a schematic block diagram illustrating the process of passing two frequency combs (e.g., near infrared light) having slightly different tooth spacings through a gas and detecting the resulting light. FIG. 1B shows the two frequency combs after the light passes through the gas, so that some light frequencies have been absorbed by the gas. FIG. 1C illustrates the resulting heterodyne interference signals at the detector, for example at rf frequencies.

DCS overcomes the key limitations of single or sparse wavelength absorption or LIDAR approaches: it enables accurate correction of the baseline laser intensity, and simultaneous measurement of $CH_4$, $^{13}CH_4$, $H_2O$, other species (such as ethane and propane), temperature, and pressure. It therefore reports interference-free, true dry-air mole fractions that account for variable water vapor dilution. With no instrument distortion (of lineshape) and a near perfect wavelength axis, the technique is also drift-free and requires no calibration. Compared with single point measurements that might be deployed on a tower or mobile platforms (aircraft or cars), this solution requires no operator involvement and can interrogate multiple locations simultaneously.

Figure 2:
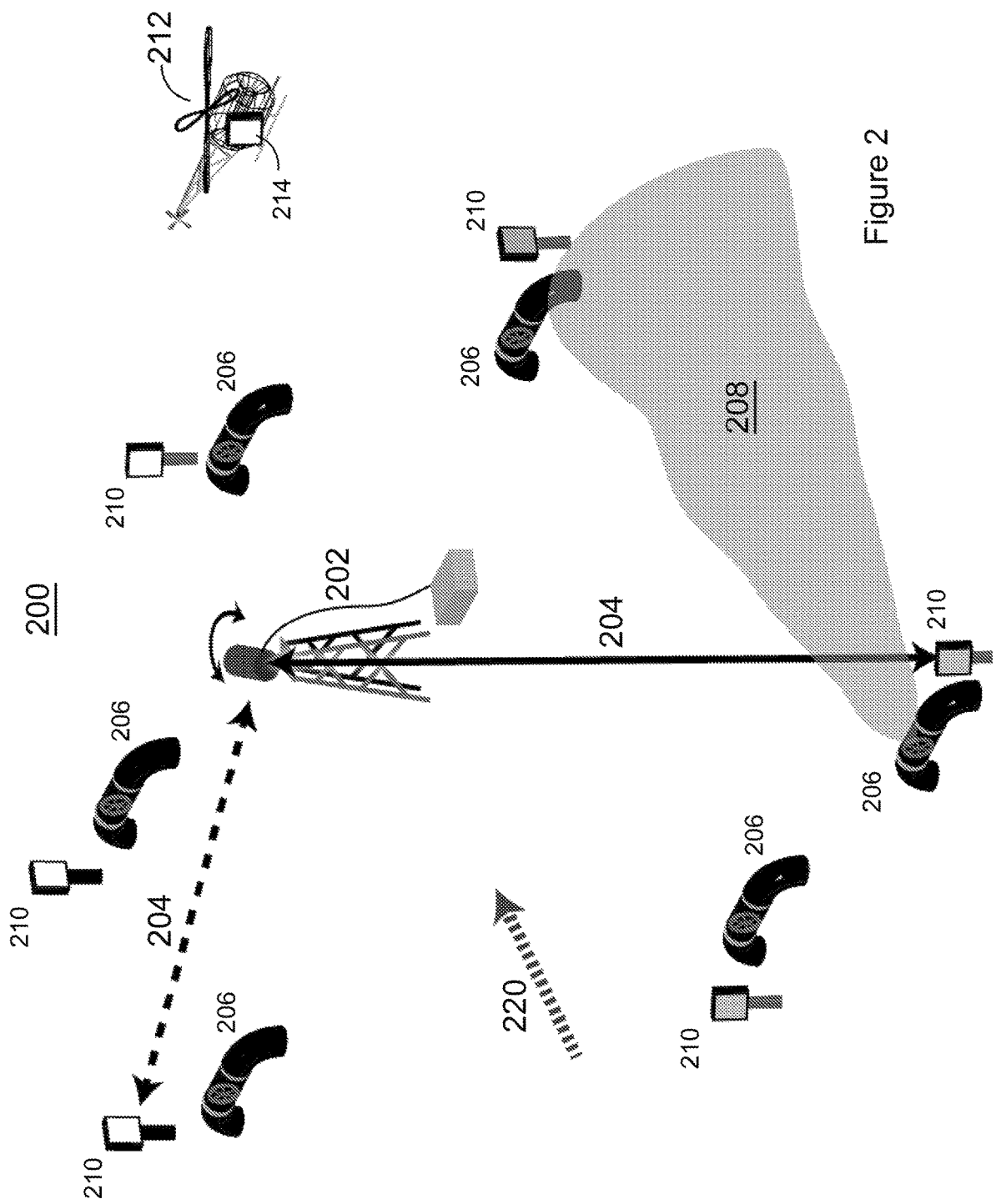
FIG. 2 is a diagram illustrating an embodiment of the data gathering portion of the present invention.

FIG. 2 is a diagram illustrating an embodiment of the data gathering portion 200 of the present invention. The open path hub-and-spoke system includes a central spectrometer/detector unit 202 and several reflectors 210 arrayed over an area to allow unit 202 to transmit and receive light in a variety of directions to detect gas 30 leaks 208 from a number of wells 206. Unit 202 scans the area with laser beams 204 over long open paths and detects the light reflected from reflectors 210. Data is generally collected over a period of days under various weather conditions.

A processor 330 (see FIGS. 3 and 4) combines the data from the reflected beams 328 with current meteorological data 340 (such as the direction and speed of wind 220) of the area to determine the location of any gas leaks. For example, processor 330 combines data from reflected beams with high-resolution computational fluid dynamics and inversion techniques to locate and size the leaks.

In some embodiments, reflectors 210 are retroreflectors which reflect the light directly back to the spectrometer/detector unit 202. Retroreflectors provide a high degree of pointing flexibility (the beams from a large array of incoming angles are redirected back the direction they came in), and thus alignment is automatic as long as the beam can track the retro-reflector.

Reflectors 210 might be located on well platforms or risers, towers, trees, fences, etc. Alternative reflectors may be used, including other fixed reflectors and even environmental reflectors such as buildings. In some embodiments, a UAV 212 with a reflector 214 periodically flies a fixed path around the area and beams 204 are reflected off reflector 214 in various directions covering the area containing wells 206.

Figure 3:
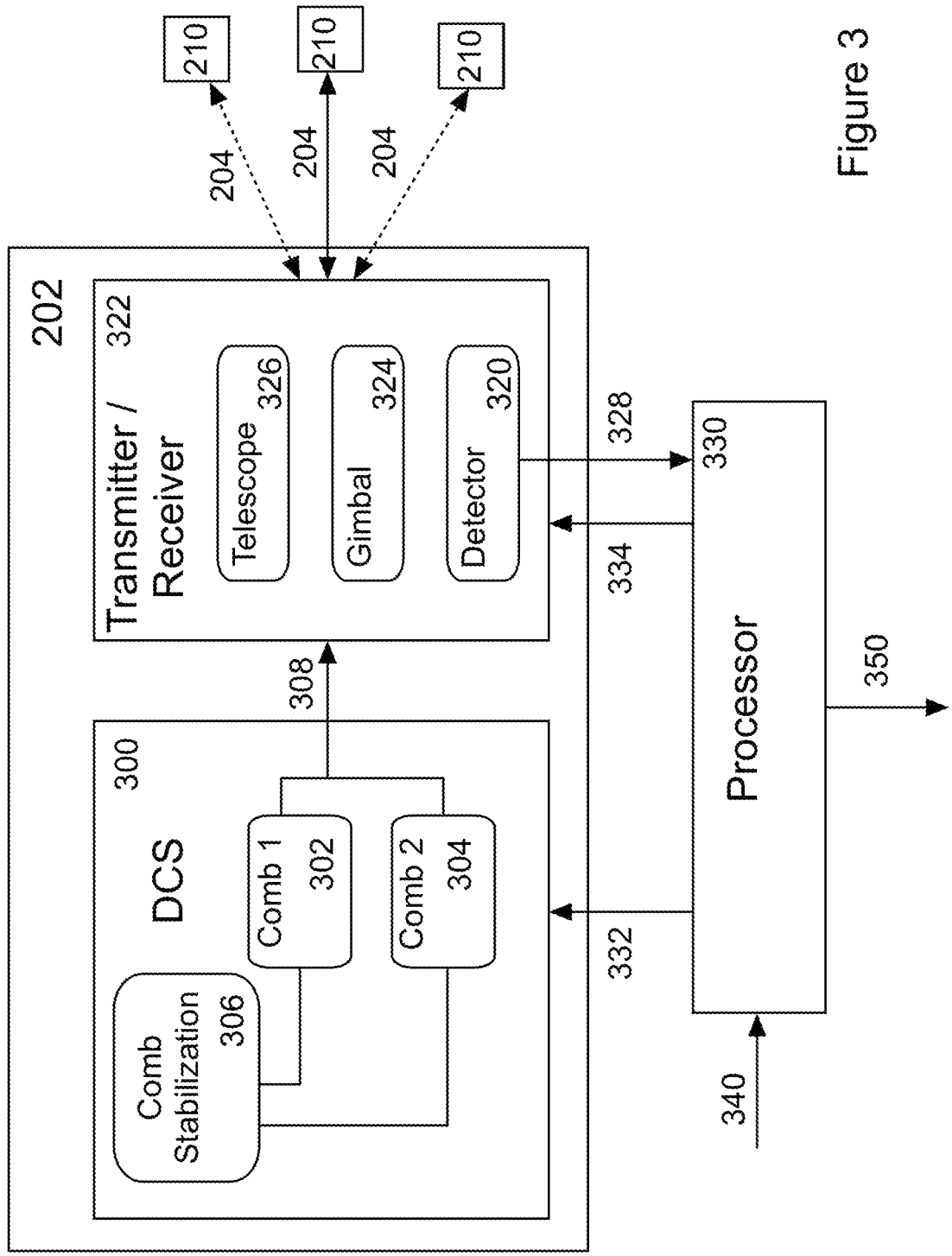
FIG. 3 is a block diagram illustrating an embodiment of the entire system according to the present invention.

One particularly useful embodiment includes a dual comb spectrometer (DCS) unit 300 (See FIG. 3). Since DCS 300 is compatible with fiber optic transmission, it is possible to monitor the perimeter of large facilities using several paths serviced by a single spectrometer via fiber optics. The same is true of multiple centralized towers separated by many kilometers. A single DCS spectrometer can supply light via optical fiber to multiple towers to reduce system cost.

In a preferred embodiment, a central, high-performance spectrometer/detector unit 202 sends light 204 sequentially over different long open paths to retroreflectors 210. The measured absorption spectra are fit to determine methane concentration enhancements. High-resolution Large Eddy Simulation-based inversion techniques are used to interpret the measured enhancement into methane leak size and location. The 1 ppb sensitivity of spectrometer/detector unit 202 enables detection of small leaks over a range of heights and downwind distances, thus enabling flexible location of retroreflectors 210. Accurate, sensitive, calibration- and drift-free measurements of methane have been demonstrated over a 2 km open air path.

FIG. 3 is a block diagram illustrating an embodiment of the entire system according to the present invention. Spectrometer/detector unit 202 transmits DCS beams 204 via transmitter/receiver 322 toward reflectors 210 and detects the reflected beams. Processor 330 combines data 328 from the reflected beams with meteorological data 340 to detect and locate any gas leaks (see FIG. 4). Meteorological data is needed to model plume shape and path of gas leaks 208.

DCS unit 300 includes two comb units 302 and 304, as well as circuitry 306 to stabilize the generated comb combination 308 and/or to electronically post-correct the spectroscopic signal 328. Combs 308 are provided to transmitter/receiver unit 322 including telescope 326 for transmitting and receiving light beams 104, gimbal 324 to scan beams 204 over the area, and detector 320 to detect the reflected beams from reflectors 210 and provide data 328 to processor 330.

Processor 330 provides control signals 332, 334 to DCS unit 300 and transmitter/receiver unit 322. It also receives reflected beam data 328 from detector 320 and meteorological data 340. Processor 330 outputs 350 the location of any gas leaks within the area.

Meteorological data 340 might comprise local measurements of wind 220, as well as temperature, humidity, etc. Alternatively, it could be determined from meteorological simulations of the area, such as WRF. Or a combination of these methods may be used.

FIG. 4A is a flow diagram illustrating a general embodiment of the signal processing portion 330 of the present invention. Meteorological data 340 are provided to a high-resolution transport model 402. High resolution transport model 402 is used to create an influence function that is passed together with spectrometer data 328 to the inversion model 404 that computes the leak location and size 350.

Standard kilometer-scale atmospheric transport models such as the widely-used Weather Research Forecast (WRF) model may not have desired resolution to locate a target leak on the meter-scale that is required by the MONITOR program. Spectrometer data can be coupled with computational fluid dynamics (CFD) model of the atmospheric transport and an inversion technique to locate and size methane leaks.

Figure 4B:
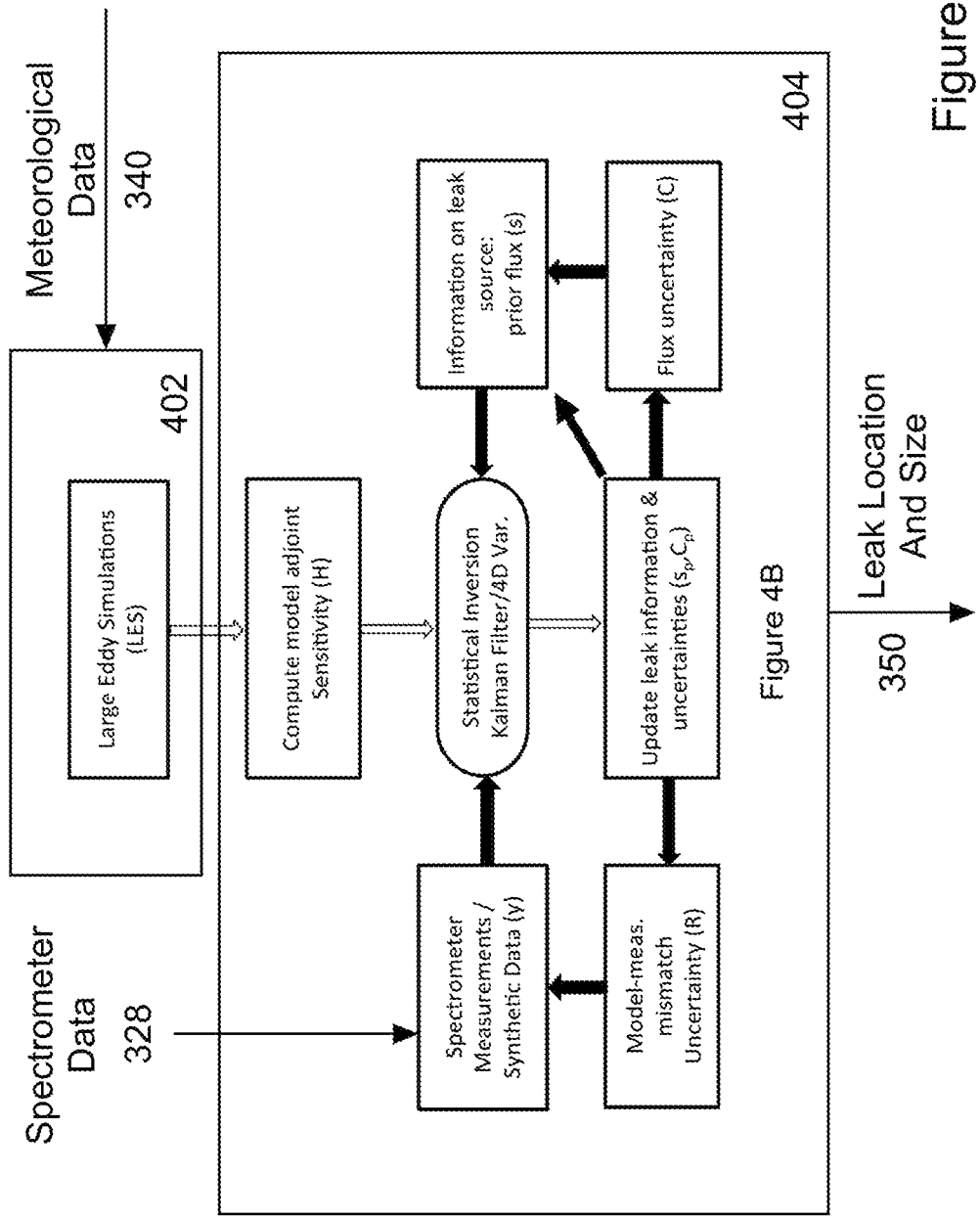
FIG. 4B is a flow diagram illustrating a specific embodiment of the preferred signal processing portion of the present invention.

FIG. 4B is a flow diagram illustrating a specific embodiment of the preferred signal processing portion of the present invention. High resolution large eddy simulations (LES) 402 incorporate the local topography (elevation, large buildings, vegetation, etc.) and local measurements of wind, temperature, and pressure for the inversion technique. Meteorological data 340 is provided as an input to the Large Eddy Simulations 402. An adjoint of the LES model is computed to determine sensitivities. These sensitivities are combined with spectrometer data as well as prior leak information to obtain updated leak information and uncertainties as part of a Kalman filtering approach 404.

The NIST Fire Dynamics Simulator (FDS) is a high-resolution CFD tool that was recently demonstrated for transport of CO2 in an urban environment. Originally developed for fire-driven flows, NIST's Fire Dynamics Simulator (FDS Version 5.5) is an open-source CFD code containing a hydrodynamic solver suitable for low-speed flow (Mach <0.3) and a thermal radiation transport model.

FDS is used mainly for large eddy simulations (LES), in which fluid motion and turbulent eddies are resolved at scales greater than the mesh cell size, while the dissipative effects of turbulence at sub-grid scales are modeled with a turbulent viscosity, rather than direct numerical simulation, which would require ~$10^{15}$ cells in a simulation domain only 100 m on a side. The LES technique might employ cells of 5 m average dimension, which requires about $7 \times 10^7$ cells to model the atmospheric boundary layer in a domain with 3 km radius.

While the exemplary preferred embodiments of the present invention are described herein with particularity, those skilled in the art will appreciate various changes, additions, and applications other than those specifically mentioned, which are within the spirit of this invention. For example, this technique could be used to locate and determine the flux of any gas source. The technique could be extended to look for other trace gasses besides methane to, for example, look for chemical leaks in industrial facilities or to, for example, look for CO2 leaks at a carbon sequestration site. Other extensions could determine emissions from industrial sites, agricultural sites, animal-raising operations, or chemical and biological weapons releases.

What is claimed is:

1. A system that determines a location and a size of a gas source within a geographic area, comprising:
   an optical source configured to transmit an optical beam to an unmanned aerial vehicle (UAV) while the UAV flies through the geographic area;
   an optical detector configured to generate path-integrated spectroscopic data from the optical beam after the UAV retroreflects the optical beam toward the optical detector while flying through the geographic area; and
   a processor configured to receive the path-integrated spectroscopic data, apply a high-resolution transport model to meteorological data for the geographic area, and apply an inversion model to the high-resolution transport model and the received path-integrated spectroscopic data to determine the location and the size of the gas source.

2. The system of claim 1, the optical beam being a dual comb spectroscopy laser beam, wherein the system implements dual comb spectroscopy of the gas source.

3. The system of claim 1, further comprising the UAV.

4. The system of claim 3, the UAV including a retroreflector configured to continuously retroreflect the optical beam while the UAV flies through the geographic area.

5. The system of claim 4, the UAV being configured to fly along a fixed path through the geographic area.

6. The system of claim 5, the UAV being configured to periodically fly along the fixed path.

7. A method that determines a location and a size of a gas source within a geographic area, comprising:
   collecting path-integrated spectroscopic data from an optical beam retroreflected by a UAV while the UAV flies through the geographic area; and
   determining the location and the size of the gas source by:
      applying a high-resolution transport model to meteorological data for the geographic area; and
      applying an inversion model to the high-resolution transport model and the collected path-integrated spectroscopic data.

8. The method of claim 7, further comprising transmitting the optical beam to the UAV while the UAV flies through the geographic area.

9. The method of claim 8, the optical beam being a dual comb spectroscopy laser beam.

10. The method of claim 8, wherein collecting the path-integrated spectroscopic data includes detecting the retroreflected optical beam while the UAV flies through the geographic area.

11. The method of claim 10, wherein determining the location and the size of the gas source includes calculating the location and the size of the gas source with a processor that also receives the path-integrated spectroscopic data.

12. The method of claim 7, further comprising retroreflecting the optical beam with the UAV while the UAV flies through the geographic area.

13. The method of claim 12, wherein retroreflecting the optical beam includes retroreflecting the optical beam with a retroreflector of the UAV.

14. The method of claim 13, further including tracking the retroreflector of the UAV, while the UAV flies through the geographic area, to set a direction of the transmitting of the optical beam to the retroreflector.

15. The method of claim 12, further comprising flying the UAV through the geographic area.

16. The method of claim 15, wherein flying the UAV through the geographic area includes flying the UAV along a fixed path through the geographic area.

17. The method of claim 16, wherein flying the UAV along a fixed path includes periodically flying the UAV along the fixed path.

18. The method of claim 15, wherein flying the UAV through the geographic area includes flying the UAV through the geographic area based on a previously-determined location and size of the gas source.

19. The method of claim 18, wherein flying the UAV through the geographic area includes flying the UAV along a path based on a previously-determined location and size of the gas source.

20. The method of claim 19, further comprising determining the path based on the previously-determined location and size of the gas source.

* * * * *